(12) United States Patent
Jörnéus

(10) Patent No.: US 6,196,842 B1
(45) Date of Patent: *Mar. 6, 2001

(54) ANCHORING ELEMENT

(75) Inventor: Lars Jörnéus, Frillesås (SE)

(73) Assignee: Nobel Biocare AB, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,520
(22) PCT Filed: May 14, 1997
(86) PCT No.: PCT/SE97/00790
§ 371 Date: Jan. 25, 1999
§ 102(e) Date: Jan. 25, 1999
(87) PCT Pub. No.: WO97/43976
PCT Pub. Date: Nov. 27, 1997

(30) Foreign Application Priority Data

May 17, 1996 (SE) .................................................. 9601913

(51) Int. Cl.[7] ........................................................ A61C 8/00
(52) U.S. Cl. .............................................................. 433/174
(58) Field of Search ............................................. 433/174

(56) References Cited

U.S. PATENT DOCUMENTS

| 5,269,685 | 12/1993 | Jörnéus ........................ 433/714 |
| 5,727,943 | 3/1998 | Beaty et al. ................... 433/174 |

FOREIGN PATENT DOCUMENTS

97/00332   1/1997   (WO) .

Primary Examiner—John J. Wilson
(74) Attorney, Agent, or Firm—Connolly Bove Lodge & Hutz

(57) ABSTRACT

An anchoring element to be screwed into a hole made in a jaw bone comprises a threaded part with a conical portion and one or more recesses in order to form a cutting edge in each recess. Thread-turn parts starting from each cutting edge are lowered vertically at the rear where they merge with a relief arranged at a distance from each cutting edge. The relief surface is arranged on the conical portion where it extends essentially parallel to a plane tangential to the conical portion.

17 Claims, 2 Drawing Sheets

_US 6,196,842 B1_

ANCHORING ELEMENT

TECHNICAL FIELD

The present invention relates to an anchoring element adapted for screwing with a tightening torque into a hole which has been made in the jaw bone. The element comprises a threaded part which has a conical (threaded) portion and one or more recesses in order to form a cutting edge in each recess. Thread-turn parts starting from each cutting edge are lowered vertically at the rear (seen in the direction of rotation) where they merge with a relief surface arranged at a distance from each cutting edge and the intended to reduce said tightening torque for the element.

BACKGROUND OF THE INVENTION

An element of the abovementioned type is already known through, for example, EP 0 530 160. The element consists of a self-tapping anchoring element which is to be screwed into a hole which has been made in the jaw bone. The element is to be capable of being used in both soft and hard jaw bone. In order to achieve good primary stability even in soft bone quality, the hole is often drilled in the jaw bone using a drill which has a small diameter in relation to the anchoring element. The surrounding soft bone material is then compressed when the anchoring element is screwed in. For hard bone, larger hole diameters are used than in the case of soft bone.

In order to provide for the above mention functions, it is important that the anchoring element has good initial self-tapping properties, i.e. to make the anchoring element "make threads" in the hard surface layer, the cortical bone, which surrounds the soft bone situated within. It is therefore unacceptable, in the case of small hole diameters in the jaw bone, to use elements with none or greatly reduced thread in the front conical part because the desired initial thread engagement is then made more difficult. It is also important, however, especially in the case of hard bone, to reduce the tightening torque, i.e. that the anchoring element has an effective relief function.

The invention aims to solve the abovementioned problems and proposes an arrangement for the conical, threaded portion which on the one hand increases the effective thread area and on the other hand provides relief functions where these are most required, i.e. where the clamping is greatest.

Along the periphery on the conical portion, each thread-turn can be considered to be lowered in the locations for the relief surfaces and the recesses. The remaining thread-turn sections around the periphery must be selected optimally according to the invention to achieve an effective initial self-tapping function. The invention solves this problem.

The heights of the thread turns above their bottom plane on the conical portion of the element can also be used in order to render the initial self-tapping property more effective. The invention also solves this problem.

An anchoring element according to the invention is mainly characterized in that each relief surface is arranged on the conical portion where it extends essentially parallel to (coincides with) a plane tangential to the conical portion.

In an advantageous embodiment, the thread in the conical portion is designed so that the inner diameter of the thread is also conically arranged, i.e. the inner diameter of the thread gradually becomes smaller as the tip is approached.

In one preferred embodiment, the number of recesses, and therefore also the number of relief surfaces, is three. The three relief surfaces are parallel to or coincide with the tangential planes. Each relief surface is preferably essentially straight.

Each thread turn can be considered to consist of remaining thread-turn sections arranged at essentially the same mutual distance from one another along the periphery on the conical portion. The sector angle for each remaining thread-turn section is selected within the range 8–20°, preferably within the range 12–15°. The sector angles for the relief surfaces correspondingly have values within the ranges of 5–15° and are preferably approximately 10°. Further developments of the invention emerge from the subclaims below.

The depth of the relief surfaces in the conical portion defines the sector angles for the remaining thread-turn sections for each thread turn around the periphery on the conical portion. Optimum anchoring elements can then be produced for use in both soft and hard bone. The thread turns, which are provided with increasingly lower height towards the front end of the element, contribute to an effective initial self-tapping property where good initial guidance of the anchoring element is possible even in the hard bone. The cutting of the threads into the jaw bone is reduced further at the tip of the conical portion. At the same time, the threaded surface area on the conical portion can, in total, be increased compared with the previously known elements. The relief functions are obtained where they are of greatest use by their positioning on the conical portion, which contributes to keeping the tightening torque low. This in turn reduces the risk of overstressing tools and/or damage or even locking fast in the surrounding hard bone material. It is essential that the anchoring element can be assigned the desired position or the desired optimum direction for the longitudinal axis of the element when it is screwed into the jaw bone.

BRIEF DESCRIPTION OF THE DRAWINGS

The presently proposed embodiment of an arrangement which has the significant characteristics of the invention is described below with simultaneous reference to the attached drawings in which.

DETAILED DESCRIPTION OF THE PREFERRED EMBODIMENT(S)

Figure 1:
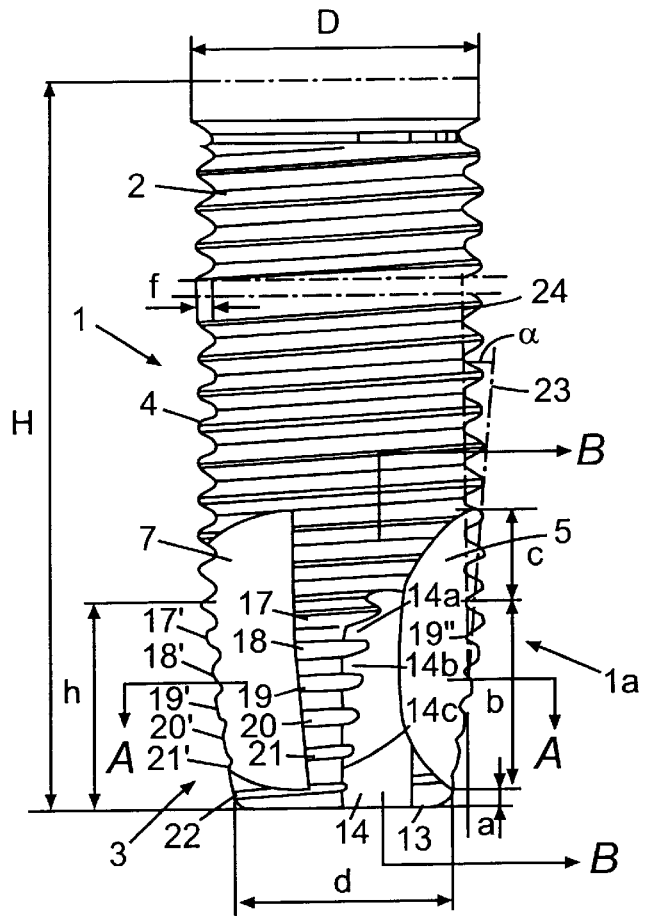
FIG. 1 shows the anchoring element in a partial vertical section, in particular its lower parts with recesses and relief surfaces and also thread-turn parts.

In FIG. 1, an anchoring element is shown by 1. The length of the element is shown by H and is preferably within the range of 10–20 mm. The element has an upper straight cylindrical part 2 and a conical part 3. Both the cylindrical part and the conical part are made with a thread 4. The cylindrical part has a diameter D which may lie within the range of 5–10 mm. The upper parts including the cylindrical part are previously known and will therefore not be described in greater detail here (refer to the above mention EP specification). The conical part has a height h of 5–10 mm and it is essential in this embodiment that the total height H can be kept low, in which connection h may be ¼–⅓ of the total height. The conical part is specially shaped according to the invention and has an average diameter d in its lowest or outermost end of 4–6 mm.

Figure 2:
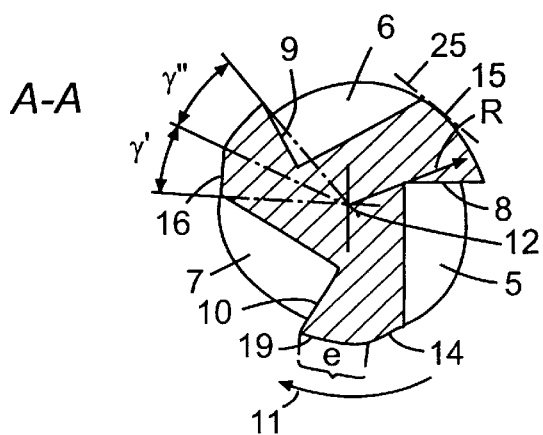
FIG. 2 shows the anchoring element according to FIG. 1 in an end section along line A—A according to FIG. 1.

In its lower parts, the anchoring element is provided with a number of recesses, in the exemplary embodiment three recesses 5, 6 and 7 (see also FIG. 2). The recesses extend downwards in the conical part and are arranged in order to form cutting edges, in this case three cutting edges 8, 9 and 10. The element is rotated in the direction of rotation of the arrow 11, i.e. in clockwise direction around the longitudinal axis 12 of the element. The recesses extend, with parts in the cylindrical part, downwards into the conical part where they run out laterally from the element at a distance a above the end surface 13 of the element. The extension along the conical part is indicated by b and the extension in the cylindrical part is indicated by c. The extension b is 2–3 times greater than the extension c. At a distance from each cutting edge, see e.g. the cutting edge 10 in FIG. 2, a relief surface 14 is arranged. The distance is indicated by e. In the present case, there are three relief surfaces 14, 15, 16 evenly distributed along the periphery on the conical part. The distances of the relief surfaces 15 and 16 from the edges 8 and 9 respectively are not specifically labelled in the figure. The height of the relief surfaces corresponds essentially to the distance a+b in the figure and the relief surfaces are thus mainly situated only on the conical part 3.

In FIG. 1, a number of thread-turn sections are indicated by 17, 18, 19, 20 and 21. Each thread-turn section has its greatest radius dimension R at the respective associated cutting edge and has a backwardly decreasing radius dimension (seen in the direction of rotation). At distance e, the thread-turn sections merge with the relief surface.

A further feature of the embodiment shown is that the thread-turn sections are assigned an increasingly lower height the closer they are situated to the end surface 13, see. thread-turn sections 17', 18', 19', 20' and 21'. Thread height in this case means a distance f from the bottom parts 19" of the thread to its upper parts 19'. FIG. 1 shows that the thread height is greatest at the upper parts on the conical portion 3 and decreases gradually to the end of the element 13.

Each relief surface 14, 15 and 16 is preferably straight and extends in between the thread turns 17, 18, 19, 20 and 21 depending on their thread heights. In this connection, the relief surface portions can be indicated as 14a, 14b, etc. An outer thread-turn section 22 only affects the respective relief surface to a limited extent. A front edge 14c on each relief surface is essentially parallel to or is inclined only slightly in relation to the vertical extension of the cutting edge (see view according to FIG. 1).

In FIG. 1, a tangential plane, which is assigned to the conical shape and extends at right angles to the figure plane according to FIG. 1, is indicated by 23. The tangential plane 23 can also be considered to extend through the bottom parts 19" of the thread-turn sections. In FIG. 1, the longitudinal direction (parallel to the longitudinal axis 12) of the element is indicated by 24. An angle α therefore represents half the cone angle which is preferably selected within the range of 2–10°, preferably the range of 3–7°.

A tangential plane corresponding to the tangential plane 23, at the relief surface 15, is indicated by 25. The relief surface 15 coincides with the tangential plane 25 which is inclined according to the tangential plane 23 above, which therefore means that the relief plane is inclined within the values indicated for the angle α.

Corresponding inclinations apply for the relief surfaces 14 and 16. The invention differs essentially in this respect from the prior art in which the relief surfaces are parallel to the longitudinal axis 12 of the element.

Figure 3:
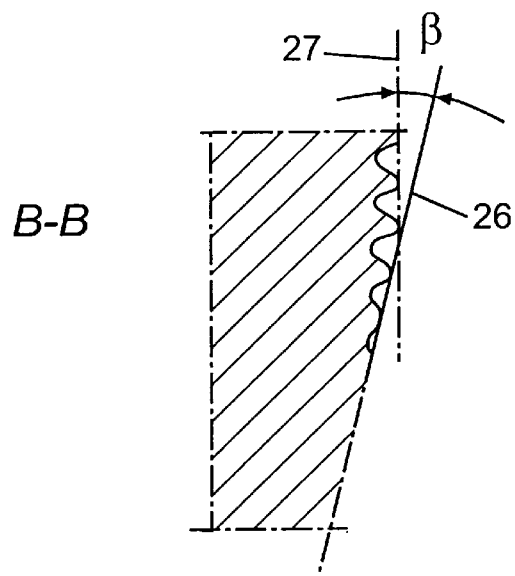
FIG. 3 shows a portion of the anchoring element in FIG. 1 in a vertical section along B—B according to FIG. 1.

In FIG. 3, a tangential plane 26 is applied over the thread-turn sections close to a cutting edge. The tangential plane 26 extends at right angles to the figure plane according to FIG. 3. A longitudinal axis parallel to the central axis 12 is indicated by 27 and the inclination between the plane 26 and the axis 27 is indicated by angles β which are in this case of the order of magnitude of 5–20°, preferably 10–15°, and therefore represent the thread-height reduction together with half the cone angle.

In FIG. 2, sector angles γ' and γ" of a relief surface and a thread-turn section respectively are indicated.

Figure 4:
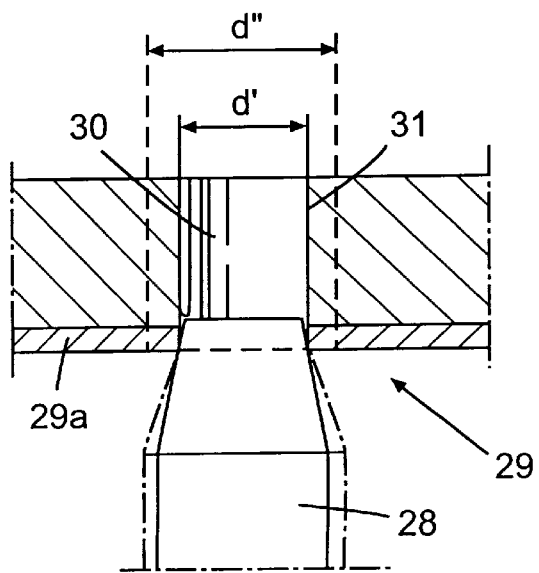
FIG. 4 shows in principle the application of the element to jaw bone in a vertical section.

In FIG. 4, the element is shown by 28 and jaw bone parts in principle by 29, which jaw bone includes a hard (cortical) layer of bone 29a. In the case of soft bone, use is made of a hole 30 with a smaller hole diameter d' and, in the case of harder bone, a hole 31 of greater hole diameter d". It is easy to see the importance of initial good interaction between the element and the bone for establishing an effective self-tapping principle.

The invention is not limited to the embodiment shown above as an example but can be subjected to modifications within the scope of the following patent claims and the inventive idea.

What is claimed is:

1. An anchoring element adapted for screwing with a tightening torque into a hole made in a bone, the anchoring element comprising a threaded member having an upper cylindrical portion and a lower conical portion, one or more recesses forming a cutting edge in the respective recesses, and thread-turn parts starting from each cutting edge and being lowered vertically at the rear for merging with a relief surface arranged at a distance from each cutting edge to reduce said tightening torque for the anchoring element, each said recess extending into both said cylindrical portion and said conical portion, a cone of the conical portion being defined by bottom parts of said thread-turn parts, and said relief surface being arranged on and confined to the conical portion where it essentially coincides with or extends parallel to a plane tangential to said cone of the conical portion.

2. An anchoring element according to claim 1, wherein the thread in the conical portion is designed so that the inner diameter of the thread is also arranged conically whereby the inner diameter of thread decreases gradually towards the tip of the element.

3. An anchoring element according to claim 2, wherein the number of recesses, and the corresponding number of relief surfaces, is selected as three and wherein said relief surfaces are parallel to or coincide with each of said tangential planes.

4. An anchoring element according to claim 2, being adapted for application in both hard and soft jaw bone material.

5. An anchoring element according to claim 2, wherein on the conical portion, a thread-turn height at each cutting edge decreases gradually in the direction of the tip of the element.

6. An anchoring element according to claim 1, wherein each relief surface is essentially straight.

7. An anchoring element according to claim 1 and having a comparatively short length which is selected within the range of 10–20 mm.

8. An anchoring element according to claim 1, wherein half the cone angle (α) for each relief surface is selected within the range of 2–10°.

9. An anchoring element according to claim 1, wherein half the cone angle (β) for the upper parts of the thread-turn parts close to each cutting edge on the conical portion is selected within the range of 5–20°.

10. An anchoring element according to claim 1, wherein each thread turn around the periphery of the conical portion consists of remaining thread-turn sections arranged at essentially the same distance from one another, and a sector angle ($\gamma''$) for each remaining thread-turn section is selected within the range of 8–20°.

11. An anchoring element according to claim 1, wherein each relief surface has a sector angle within the range of 5–15°.

12. An anchoring element according to claim 1, wherein each relief surface is lowered in the material of the conical portion and extends in part between the backwardly decreasing thread-turns.

13. An anchoring element according to claim 1, wherein said relief surface extends into an end surface of said conical portion.

14. An anchoring element according to claim 1, wherein half the cone angle ($\alpha$) for each relief surface is selected within the range of 3–7°.

15. An anchoring element according to claim 1, wherein half the cone angle ($\beta$) for the upper parts of the thread-turn parts close to each cutting edge on the conical portion is selected within the range of 10–15°.

16. An anchoring element according to claim 1, wherein each thread turn around the periphery of the conical portion consists of remaining thread-turn sections arranged at essentially the same distance from one another, and a sector angle ($\gamma''$) for each remaining thread-turn section is selected within the range of 12–15°.

17. An anchoring element according to claim 1, wherein each relief surface has a sector angle of approximately 10°.

* * * * *